United States Patent [19]  [11] 4,035,507
Bodor et al.  [45] July 12, 1977

[54] NOVEL, TRANSIENT PRO-DRUG FORMS OF L-DOPA TO TREAT PARKINSON'S DISEASE

[75] Inventors: Nicolae S. Bodor; Kenneth B. Sloan, both of Lawrence, Kans.; Anwar A. Hussain, Lexington, Ky.

[73] Assignee: Interx Research Corporation, Lawrence, Kans.

[21] Appl. No.: 708,285

[22] Filed: July 23, 1976

Related U.S. Application Data

[60] Division of Ser. No. 569,009, April 17, 1975, Pat. No. 3,998,799, which is a continuation-in-part of Ser. No. 412,419, Nov. 2, 1973, Pat. No. 3,891,696.

[51] Int. Cl.² .............. A61K 31/22; A61K 31/24; A61K 31/195
[52] U.S. Cl. .............................. 424/311; 424/319
[58] Field of Search .......... 424/319, 263, 311, 264, 424/309

Primary Examiner—Stanley J. Friedman
Attorney, Agent, or Firm—Charles N. Blitzer

[57] ABSTRACT

There is provided, novel, transient pro-drug forms of L-DOPA (3,4-dihydroxy-L-phenylalanine), having the formula:

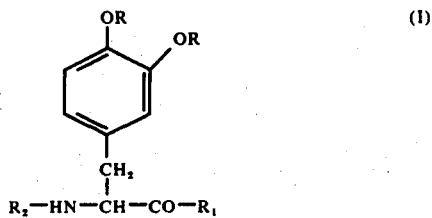

wherein R represents a hydrogen atom, an acyl group, a

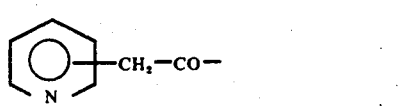

group, a -CO-pyridyl group, and a -CO-R$_3$ group, wherein R$_3$ represents the residue of any N,N-C$_1$-C$_2$ dialkylamino acid or a C$_4$-C$_6$ cycloalkylamino acid

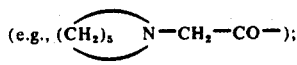

wherein R$_1$ represents a member selected from the group consisting of a hydroxyl group and a —OM group, wherein M is an alkali metal (Na, K, etc.) or an ammonium ion; and wherein R$_2$ represents a member selected from the group consisting of a

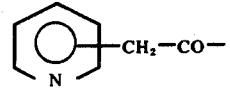

group, a -CO-pyridyl group, and a —CO-R$_3$ group, wherein R$_3$ represents the residue of any N,N-(C$_1$-C$_2$)—dialkylamino acid or a C$_4$-C$_6$-cycloalkylamino acid

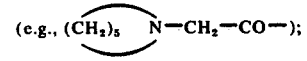

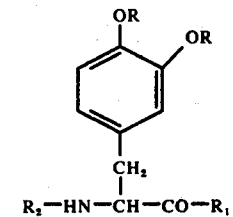

wherein R represents an acyl group; wherein R$_2$ represents a hydrogen atom; and wherein R$_1$ represents a —NHCH(R$_4$)COOR$_5$ group, wherein R$_4$ represents the residue of any naturally occurring amino acid, and wherein R$_5$ represents a member selected from the group consisting of a hydrogen atom, a C$_1$-C$_5$ alkyl group (e.g., methyl, ethyl, propyl, butyl, pentyl), and a C$_1$-C$_5$ alkylaryl group (e.g., —CH$_2$-C$_6$H$_5$, —CH$_2$-CH$_2$—C$_6$H$_5$, etc.), and the HX salts thereof, wherein X is a conventional pharmaceutically acceptable acid addition salt anion (e.g., chloride, bromide, perchlorate, methanesulfonate, succinate, etc.);

(III)

wherein R represents an acyl group; wherein R$_1$ represents a member selected from the group consisting of a hydroxyl group, a —OCH$_3$ group, a —OC$_2$H$_5$ group, a —OC$_3$H$_7$ group, a —OC$_4$H$_9$ group, and a -OCH$_2$-C$_6$H$_5$ group; and wherein R$_2$ represents an NH$_2$CH(R$_6$)CO— group, wherein R$_6$ represents the residue of any naturally occurring amino acid, and the HX salts thereof, wherein X is defined as above;

(IV)

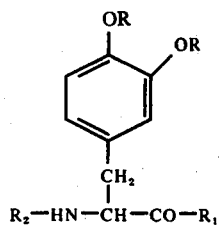

wherein R represents a member selected from the group consisting of an acyl group; wherein $R_1$ represents a member selected from the group consisting of a hydroxyl group, a $-OCH_3$ group, a $-OC_2H_5$ group, a $-OC_3H_7$ group, a $-OC_4H_9$ group, and a $-OCH_2-C_6H_5$ group; and wherein $R_2$ represents an $NH_2-CH(R_7)-CO-$ group, wherein $R_7$ represents the residue of a 3,4-L-diacylphenylalanine group having the formula:

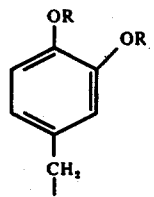

wherein R is defined as above, and the HX salts thereof, wherein X is as defined above; and

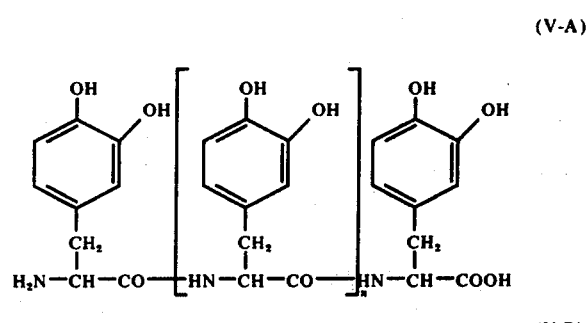

(V-A)

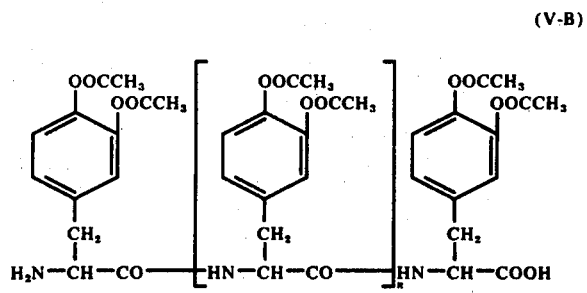

(V-B)

wherein $n$ represents an integer of from 2 to 50 with respect to formula (V-A), and wherein $n$ represents an integer of from 1 to 50 with respect to formula (V-B).

These compounds are all useful in the treatment of Parkinson's Disease.

109 Claims, No Drawings

NOVEL, TRANSIENT PRO-DRUG FORMS OF L-DOPA TO TREAT PARKINSON'S DISEASE

This application is a divisional application of our earlier copending application Ser. No. 569,009, filed April 17, 1975, now U.S. Pat. No. 3,998,799 which in turn is a continuation-in-part application Ser. No. 412,419, filed Nov. 2, 1973, now U.S. Pat. No. 3,891,696.

BACKGROUND OF THE INVENTION

1. Field of the Invention

The present invention is directed to L-DOPA type compounds and more specifically, to certain novel, transient, pro-drug forms of L-DOPA, capable of administration to warm-blooded animals.

As employed in this application, the expression "pro-drug" denotes a derivative of a known and proven prior art compound, which derivative, when absorbed into the bloodstream of a warm-blooded animal, "cleaves" in such a manner as to release the proven drug form and permit the same to attain a higher bioavailability level than that which could be obtained if the proven drug form per se was administered.

Furthermore, as used in this application, the term "transient" denotes "cleavage" of the compounds of this invention in such a manner that the proven drug form is released and the remaining "cleaved" moiety is non-toxic and metabolized in such a manner that non-toxic, metabolic products are produced.

2. Description of the Prior Art

L-DOPA (3,4-dihydroxy-L-phenylalanine) is presently, generally accepted as the primary drug of choice in the treatment of Parkinson's Disease. However, due to its extensive extracerebral metabolism, extremely large doses (up to 8 grams) of this drug are required to initiate a medically acceptable therapeutic effect. Such large doses often cause intolerable side effects, such as gastro-intestinal symptoms (anorexia, nausea, and vomiting), orthostatic hypotension, and the development of involuntary movements. See, D. B. Calne, *Clin. Pharmac. Ter.*, 11, 789 (1971). While decreasing the daily dose of L-DOPA would eliminate the above-described side effects, nevertheless, Parkinsonism symptons will return.

It has been known that a significant percentage of the amount of L-DOPA in contact with the gastric mucosa is metabolized (L. Rivera-Calimlim, C. A. Dujovane, J. P. Morgan, L. Lasagna, and J. R. Bianchine, *Europ. J. Clin. Invest.*, 1, 313 (1971). This may delay and lower the attainable peaks of unchanged L-DOPA in the blood serum, which may be a critical factor for the passage of L-DOPA into the brain. Although, possibly, some metabolism of L-DOPA can occur in the human intestine, it would be expected to be minimal, because L-DOPA appears to be more rapidly absorbed in the intestine. On the other hand, L-DOPA, once delivered to the bloodstream by any suitable route (orally) is rapidly and continuously metabolized, since only 5.0 to 8.0 percent of L-DOPA is protein bound. Consequently, L-DOPA is very susceptible to metabolic processes. See, H. Hinterberger, *Biochem. Med.*, 5, 412 (1971).

The metabolism of L-DOPA can occur through a wide variety of metabolic pathways. The main initial steps are decarboxylation, 3-O-methylation, or transamination. L-DOPA appears to be metabolized within the brain in the same manner, as it is extracerebally metabolized. The necessary enzymes required to achieve these metabolisms, are DOPA-decarboxylase, COMT and MAO. These enzymes are well-known and widely distributed in man, including the liver, kidney, heart, and brain.

Due to the short half-life of L-DOPA in the bloodstream (approximately 45 minutes) as determined by C. B. Coutinaho, H.E. Spiegel, et al., *J. Pharm. Sci.*, 60, 1014 (1971) and B. Weiss, and G. V. Rossi, *Biochem Pharmacol.*, 12, 1399 (1963), and further due to its excessive metabolism prior to distribution in the bloodstream, a means of increasing L-DOPA blood levels without increasing L-DOPA dosage becomes exceedingly necessary.

The initial approach to this problem resides in decreasing the stomach elimination time, usually through the use of antacids, which appear to decrease gastric distress and result in somewhat higher L-DOPA blood levels. See, J. R. Bianchine, L. Rivera-Calimlin, C. A. Dujovene, J. P. Morgan, and L. Lasagne, *Ann. N.Y. Acad. Sci.*, 179, 126 (1971).

In other instances, the employment of decarboxylase inhibitors appear to provide some improvement. For example, reference is made to the articles by A. Pletscher and C. Bartholini, *Clin. Pharmac. Ther.*, 12, 344 (1971); D. L. Dunner, H.U.H. Brodie, and F. K. Goodwin, Ibid, 12, 212 (1971); and A. Barbeau, L. Gillo-Goffrey and H. Mars, Ibid, 12, 353 (1971).

With respect to the above, the most potent decarboxylase inhibitors are those of the hydrazine type, such as RO4-4602 [N-(D,L-Seryl)-N'-(2,3,4-trihydroxybenzyl)-hydrazine] and MK-486 (alphamethyl-dopa-hydrazine). By employing these inhibitors, relatively small dosages of L-DOPA will provide therapeutic blood levels; however, the patient may be subjected to toxic effects as a result of such inhibitors.

It has also been found that the co-administration of COMT (catechol-O-methyl-transferase) inhibitors can also result in an increase in the free L-DOPA blood level. See, R. D. Robson, N.J. Antonaccio, and R. K. Reinhart, *Europ. J. Pharmacol.*, 20, 104 (1972) and R. J. Valdessarini, and E. Greiner, *Biochem. Pharmacol.*, 22, 247 (1973). With reference to these articles, it was determined that L-DOPA can severely tax normal methylation processes and therefore, interfere with methylation of biologically important substances. Moreover, it has also been determined that L-DOPA can increase blood concentrations of SAMe (s-adenosyl-methionine) in patients treated.

Therefore, it follows that blocking the methylation of L-DOPA might enhance bioavailability thereof, decrease the formation of methylated metabolites and further prevent the occurrence of side effects associated with L-DOPA.

It has been demonstrated that the COMT inhibitors, do indeed aid in the reduction of the therapeutic dose required for L-DOPA. However, most of the available COMT inhibitors, including pyrogallol, desmethyl-papaverine, tropolones, catecholacetamides, gallic acid esters, and substituted benzoates are of limited utility because of their lack of potency and duration of action, or in the alternative, simply due to their extreme toxicity.

Recently, U.S. Pat. No. 3,803,120 issued disclosing and claiming certain unprotected di- and tri-peptides of L-DOPA. While the patentee does disclose fully unprotected di- and tri-peptides of L-DOPA, therapeutically active protected di- and tri-peptides of L-DOPA are not at all suggested. As indicated earlier, the essence of this invention relies on the fact that three sites of unwanted metabolism are present on the L-DOPA molecule. Consequently, according to this invention, these metabolic sites are protected during and/or prior to the absorption process. In this manner, degradation of the L-DOPA molecule will not occur at a point in time where it would hinder the attainment of L-DOPA bioavailability. Evidence of the superior advantage attained with protecting the L-DOPA molecule in this manner is easily gathered from a review of Table I of this application. In all instances, the protected L-DOPA compounds of this invention enabled L-DOPA to obtain superior bioavailability levels in comparison to that obtained when L-DOPA was administered per se. Granted, the patentee does disclose a protected L-DOPA molecule in numerous instances, but in each of these instances, it is for the sole purpose of protecting the L-DOPA molecule during synthesis. That is, the protected L-DOPA compounds of the patentee are useful as intermediates only. This is further buttressed by the fact that the patentee specifically teaches that only compounds of the formula (I) through (IV) and (XX) have any anti-Parkinsonism activity at all. The compounds encompassed within the aforementioned formulas of the patentee do not represent fully protected L-DOPA compounds as is the case with the instant invention. See also, "Synthesis and Antireserpine Activity of Peptides of L-DOPA", Arthur M. Felix, et al., J. Med. Chem., 17, No. 4, 422 (1974).

SUMMARY OF THE INVENTION

It is one object of the present invention to provide novel, transient, pro-drug forms of L-DOPA, useful in the treatment of Parkinson's Disease in warm-blooded animals.

It is another object of the present invention to provide novel, transient, pro-drug forms of L-DOPA, which cleave in such a manner as to enable the original proven drug form (L-DOPA) to be released in the bloodstream of a warm-blooded animal and to further permit the cleaved moiety(ies), unassociated with the proven drug form to be non-toxic and metabolized in a non-toxic fashion.

Still, it is another object of the present invention to provide novel, transient, pro-drug forms of L-DOPA which, owing to their high solubility and/or better absorption properties, enable high blood levels of L-DOPA to be attained, following cleavage of the pro-drug form.

Finally, it is yet another object of the present invention to provide novel, transient, pro-drug forms of L-DOPA, which exhibit superior bioavailability over L-DOPA per se, when administered orally in a pharmaceutically acceptable oral dosage form. That is, applicants have concerned themselves with producing oral pro-drug forms of L-DOPA which would permit high blood levels of L-DOPA to be attained, but wherein the dose of the pro-drug form required to achieve a sufficient therapeutic effect is less than the therapeutic dose required of L-DOPA per se.

Accordingly, all the foregoing objects are realized through the use of certain selected novel, transient pro-drug forms of L-DOPA having the formula:

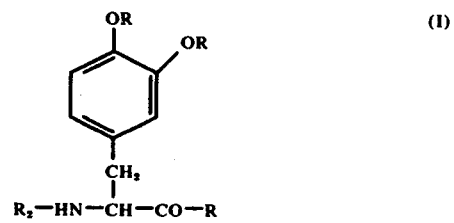

wherein R represents a hydrogen atom, an acyl group

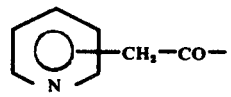

group, a -CO-pyridyl group, and a -CO-$R_3$ group, wherein $R_3$ represents the residue of any N,N-$C_1$-$C_2$ dialkylamino acid or a $C_4$-$C_6$ cycloalkylamino acid (e.g., $(CH_2)_5$ N—$CH_2$—CO—);

wherein $R_1$ represents a member selected from the group consisting of a hydroxyl group and a -OM group, wherein M is an alkali metal (Na, K, etc.) or an ammonium ion; and wherein $R_2$ represents a member selected from the group consisting of a

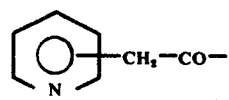

group, a -CO-pyridyl group, and a -CO-$R_3$ group, wherein $R_3$ represents the residue of any N,N-($C_1$-$C_2$)dialkylamino acid or a $C_4$-$C_6$-cycloalkylamino acid (e.g., $(CH_2)_5$ N—$CH_2$—CO—);

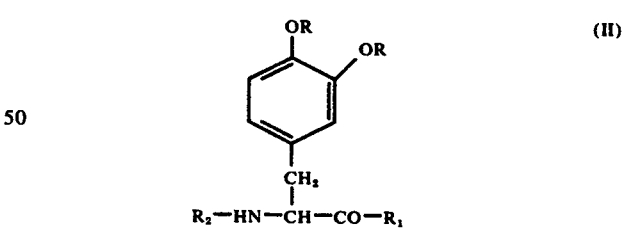

wherein R represents an acyl group; wherein $R_2$ represents a hydrogen atom; and wherein $R_1$ represents a —NHCH($R_4$)COO$R_5$ group, wherein $R_4$ represents the residue of any naturally occurring amino acid, and wherein $R_5$ represents a member selected from the group consisting of a hydrogen atom, a $C_1$-$C_5$ alkyl group (e.g., methyl, ethyl, propyl, butyl, pentyl), and a $C_1$-$C_5$ alkylaryl group (e.g., —$CH_2$—$C_6H_5$, -$CH_2$-$CH_2$-$C_6H_5$, etc.), and the HX salts thereof, wherein X is a conventional pharmaceutically acceptable acid addition salt anion (e.g., chloride, bromide, perchlorate, methanesulfonate, succinate, etc.);

(III)

[Structure: benzene ring with OR, OR substituents and CH₂ group connected to R₂—HN—CH—CO—R₁]

wherein R represents an acyl group; wherein $R_1$ represents a member selected from the group consisting of a hydroxyl group, a —$OCH_3$ group, a —$OC_2H_5$ group, a —$OC_3H_7$ group, a —$OC_4H_9$ group, and a —$OCH_2$-$C_6H_5$ group; and wherein $R_2$ represents an $NH_2CH(R_6)CO$— group, wherein $R_6$ represents the residue of any naturally occurring amino acid, and the HX salts thereof, wherein X is defined as above;

(IV)

[Structure: benzene ring with OR, OR substituents and CH₂ group connected to R₂—HN—CH—CO—R₁]

wherein R represents a member selected from the group consisting of an acyl group; wherein $R_1$ represents a member selected from the group consisting of a hydroxyl group, a —$OCH_3$ group, a —$OC_2H_5$ group, a —$OC_3H_7$ group, a —$OC_4H_9$ group, and a —$OCH_2$-$C_6H_5$ group; and wherein $R_2$ represents an $NH_2$-$CH(R_7)$-$CO$- group, wherein $R_7$ represents the residue of a 3,4-L-diacylphenylalanine group having the formula:

[Structure: benzene ring with OR, OR substituents and CH₂ group]

wherein R is defined as above, and the HX salts thereof, wherein X is as defined above; and (V-A)

[Structure: H₂N—CH—CO—[HN—CH—CO]—HN—CH—COOH with three benzene rings bearing OH, OH groups linked via CH₂]

(V-B)

[Structure: H₂N—CH—CO—[HN—CH—CO]—HN—CH—COOH with three benzene rings bearing OOCCH₃, OOCCH₃ groups linked via CH₂]

wherein n represents an integer of from 2 to 50 with respect to formula (V–A), and wherein n represents an integer of from 1 to 50 with respect to formula (V-B).

In the above formulas, reference to "acyl" refers to any straight, branched or aromatic acyl group capable of cleaving enzymatically and/or chemically, in vivo. This term thus includes without limitation -$COCH_3$, —$COC_2H_5$, —$COOC_2H_5$, —CO-C($CH_3$)$_3$, —$COC_5H_{11}$, —$COC_8H_{17}$, —$COC_{12}H_{25}$, —$COC_{15}H_{31}$, —$COC_{20}H_{41}$, benzoyl, toloyl, xyloyl, etc.. Reference to "naturally occurring amino acid," refers to any naturally occurring amino acid including, without limitation, glycine, alanine, valine, leucine, isoleucine, cysteine, cystine, methionine, serine, threonine, aspartic acid, glutamic acid, arginine, leucine, hydroxylsine, phenylalanine, tyrosine, asparagine, glutamine, proline, hydroxyproline, histidine, tryptophan, pyroglutamic acid, etc.

At this point in time, it is noteworthy to mention that applicants' approach to improving the oral bioavailability of L-DOPA differs from the approaches taken by the prior art today. As applicants could determine, by partially inhibiting the main metabolic pathways of L-DOPA through coadministration of decarboxylase inhibitors and/or COMT inhibitors, higher L-DOPA levels could be achieved, using smaller therapeutic doses. However, applicants also observed that these approaches had their limitations and specifically, the toxicity of the enzymatic inhibitors employed at the necessary high dosage level required. Thus, while the use of such inhibitors might achieve the ultimate therapeutic result, the therapeutic dosage required of these inhibitors to achieve this result is so demanding that toxicity factors come into play.

Therefore, applicants' approach was to develop transient derivatives of L-DOPA which would exhibit a higher absorption rate (mainly due to their higher water and/or lipid solubility) and at the same time, derivatives which would be less susceptible to extensive metabolism prior to and/or during the absorption process.

These derivatives were realized by placing protective groups on the reactive sites of the L-DOPA molecule; the catechol system, the amino and/or carboxy group. Therefore, the transient derivatives of L-DOPA proposed herein can delivery L-DOPA at high blood levels after a chemical and/or enzymatic hydrolysis, and yet, at a lesser dosage level than that required for L-DOPA, per se. Moreover, once the derivatives of this invention are cleaves so as to release L-DOPA, the cleaved moiety(ies), other than the L-DOPA moiety, will be metabolized into non-toxic products as a result of the protective groups placed on the reactive site of the L-DOPA molecule. Furthermore, the aforementioned cleaved moiety is non-toxic, per se.

At this junction, it is interesting to further note that other individuals have suggested the use of possible pro-drug forms of L-DOPA, such as the simple aliphatic esters thereof. However, they have reported only the D, L-DOPA esters. See, C. H. M. Lai and W. D. Mason, J. Pharm. Sci., 62, 511 (1973). In addition, the N-acetyl-L-DOPA esters have also been disclosed (see, Japanese Pat. Nos. 34,334/1972 and 34,335/1972), respectively. However, these compounds do not exhibit the properties observed with the compounds of the instant invention. Among the compounds encompassed within the above generic formulae, certain compounds are, nevertheless, preferred. However, in any event, all compounds encompassed within the above generic formulae meet applicants' criteria as outlined earlier, and are superior to L-DOPA, per se in terms of solubility or absorption and/or bioavailability.

DETAILED DESCRIPTION OF THE INVENTION

Therefore, the following compounds represent those compounds preferred among all the compounds encompassed within the abovedescribed generic formulae:

1. Glycyl-3,4-diacetyloxy-L-phenylalanine and its HX salt, wherein X represents a pharmaceutically acceptable anion.
2. Glycyl-3,4-diacetyloxy-L-phenylalanine-methyl ester and its HX salt, wherein X represents a pharmaceutically acceptable anion.
3. 3,4-diacetyloxy-L-phenylalanyl-glycine and its HX salt, wherein X represents a pharmaceutically acceptable anion.
4. N-nicotinoyl-3,4-dihydroxy-L-phenylalanine and its M salt, wherein M represents an alkali metal.
5. N-nicotinoyl-3,4-diacetyloxy-L-phenylalanine and its M salt, wherein M represents an alkali metal.
6. N-nicotinoyl-3,4-dipivalyloxy-L-phenylalanine and its M salt, wherein M represents an alkali metal.
7. 3,4-diacetyloxy-L-phenylalanyl-glycine and its HX salt, wherein X represents a pharmaceutically acceptable anion.
8. 3,4-diacetyloxy-L-phenylalanyl-glycine-methyl ester and its HX salt, wherein X represents a pharmaceutically acceptable anion.
9. 3,4-diacetyloxy-L-phenylalanyl-glycine-ethyl ester and its HX salt, wherein X represents a pharmaceutically acceptable anion.
10. 3,4-diacetyloxy-L-phenylalanyl-glycine-benzyl ester and its HX salt, wherein X represents a pharmaceutically acceptable anion.
11. 3,4-diacetyloxy-L-phenylalanyl-L-leucine and its HX salt, wherein X represents a pharmaceutically acceptable anion.
12. 3,4-diacetyloxy-L-phenylalanyl-L-leucine-methyl ester and its HX salt, wherein X represents a pharmaceutically acceptable anion.
13. 3,4-diacetyloxy-L-phenylalanyl-L-leucine-ethyl ester and its HX salt, wherein X represents a pharmaceutically acceptable anion.
14. 3,4-diacetyloxy-L-phenylalanyl-L-leucine-benzyl ester and its HX salt, wherein X represents a pharmaceutically acceptable anion.
15. 3,4-diacetyloxy-L-phenylalanyl-L-isoleucine and its HX salt, wherein X represents a pharmaceutically acceptable anion.
16. 3,4-diacetyloxy-L-phenylalanyl-L-isoleucine-methyl ester and its HX salt, wherein X represents a pharmaceutically acceptable anion.
17. 3,4-diacetyloxy-L-phenylalanyl-L-isoleucine-ethyl ester and its HX salt, wherein X represents a pharmaceutically acceptable anion.
18. 3,4-diacetyloxy-L-phenylalanyl-L-isoleucine-benzyl ester and its HX salt, wherein X represents a pharmaceutically acceptable anion.
19. 3,4-diacetyloxy-L-phenylalanyl-phenylalanine and its HX salt, wherein X represents a pharmaceutically acceptable anion.
20. 3,4-diacetyloxy-L-phenylalanyl-phenylalanine-methyl ester and its HX salt, wherein X represents a pharmaceutically acceptable anion.
21. 3,4-diacetyloxy-L-phenylalanyl-phenylalanine-ethyl ester and its HX salt, wherein X represents a pharmaceutically acceptable anion.
22. 3,4-diacetyloxy-L-phenylalanyl-phenylalanine-benzyl ester and its HX salt, wherein X represents a pharmaceutically acceptable anion.
33. Glycyl-3,4-diacetyloxy-L-phenylalanine and its HX salt, wherein X represents a pharmaceutically acceptable anion.
24. Glycyl-3,4-dipivalyloxy-L-phenylalanine and its HX salt, wherein X represents a pharmaceutically acceptable anion.
25. Glycyl-3,4-diacetyloxy-L-phenylalanine-methyl ester and its HX salt, wherein X represents a pharmaceutically acceptable anion.
26. Glycyl-3,4-diacetyloxy-L-phenylalanine-ethyl ester and its HX salt, wherein X represents a pharmaceutically acceptable anion.
27. Glycyl-3,4-diacetyloxy-L-phenylalanine-benzyl ester and its HX salt, wherein X represents a pharmaceutically acceptable anion.
28. L-leucyl-3,4-diacetyloxy-L-phenylalanine and its HX salt, wherein X represents a pharmaceutically acceptable anion.
29. L-leucyl-3,4-diacetyloxy-L-phenylalanine-methyl ester and its HX salt, wherein X represents a pharmaceutically acceptable anion.
30. L-leucyl-3,4-diacetyloxy-L-phenylalanine-ethyl ester and its HX salt, wherein X represents a pharmaceutically acceptable anion.
31. L-leucyl-3,4-diacetyloxy-L-phenylalanine-benzyl ester and its HX salt, wherein X represents a pharmaceutically acceptable anion.
32. L-isoleucyl-3,4-diacetyloxy-L-phenylalanine and its HX salt, wherein X represents a pharmaceutically acceptable anion.
33. L-isoleucyl-3,4-diacetyloxy-L-phenylalanine-methyl ester and its HX salt, wherein X represents a pharmaceutically acceptable anion.
34. L-isoleucyl-3,4-diacetyloxy-L-phenylalanine-ethyl ester and its HX salt, wherein X represents a pharmaceutically acceptable anion.
35. L-isoleucyl-3,4-diacetyloxy-L-phenylananine-benzyl ester and its HX salt, wherein X represents a pharmaceutically acceptable anion.
36. Phenylalanyl-3,4-diacetyloxy-L-phenylalanine and its HX salt, wherein X represents a pharmaceutically acceptable anion.
37. Phenylalanyl-3,4-diacetyloxy-L-phenylalanine-methyl ester and its HX salt, wherein X represents a pharmaceutically acceptable anion.
38. Phenylalanyl-3,4-diacetyloxy-L-phenylalanine-ethyl ester and its HX salt, wherein X represents a pharmaceutically acceptable anion.

39. Phenylalanyl-3,4-diacetyloxy-L-phenylalanine-benzyl ester and its HX salt, wherein X represents a pharmaceutically acceptable anion.
40. 3,4-diacetyloxy-L-phenylalanyl-3,4-diacetyloxy-L-phenyl-alanine and its HX salt, wherein X represents a pharmaceutically acceptable anion.
41. 3,4-diacetyloxy-L-phenylalanyl-3,4-diacetyloxy-L-phenyl-alanine-methyl ester and its HX salt, wherein X represents a pharmaceutically acceptable anion.
42. 3,4-diacetyloxy-L-phenylalanyl-3,4-diacetyloxy-L-phenyl-alanine-ethyl ester and is HX salt, wherein X represents a pharmaceutically acceptable anion.
43. 3,4-diacetyloxy-L-phenylalanyl-3,4-diacetyloxy-L-phenyl-alanine-benzyl ester and its HX salt, wherein X represents a pharmaceutically acceptable anion.
44. Poly 3,4-dihydroxy-L-phenylalanine:

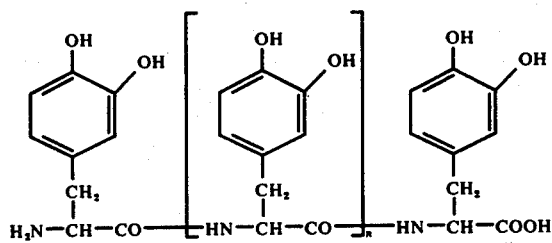

wherein n represents an integer of 7 – 20.
45. Poly-3,4-diacetoxy-L-phenylalanine:

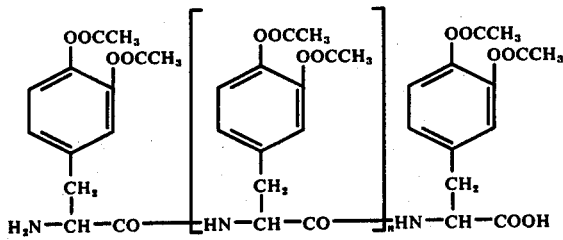

wherein n represents an integer of 7 – 20.
46. N-[N,N-dimethylamino]-glycyl-3,4-dihydroxy-L-phenyl-alanine and its M salt, wherein M represents an alkali metal.
47. N-[N,N-dimethylamino]-glycyl-3,4-diacetyloxy-L-phenylalanine and its M salt, wherein M represents an alkali metal.
48. N-nicotinoyl-3,4-dinicotinoyloxy-L-phenylalanine and its M salt, wherein M represents an alkali metal.
49. N-3-pyridylacetyl-3,4-dihydroxy-L-phenylalanine and its M salt, wherein M represents an alkali metal.
50. N-3-pyridylacetyl-3,4-diacetyloxy-L-phenylalanine and its M salt, wherein M represents an alkali metal.
51. 3,4-N,N-dimethylaminoglycyl-L-phenylalanine methyl-ester and its HX salt, wherein X represents a pharmaceutically acceptable anion.
52. N-[N,N-dimethylamino]glycyl-3,4-[N,N-dimethylaminoglycyl]-L-phenylalanine and its M salt, wherein M represents an alkali metal.
53. N-[N,N-diethylaminoglycyl]-3,4-diacetyloxy-L-phenylalanine and its M salt, wherein M represents an alkali metal.

The compounds encompassed within the above recited generic formulae can be essentially grouped into five (5) classes, as described hereinafter. These will be referred to as Classes (I) through (V), respectively.

THE COMPOUNDS OF CLASS (I)

The compounds of this class constitute some amides of 3,4-diacylated L-DOPA, wherein R represents a member selected from the group consisting of an acyl group, a

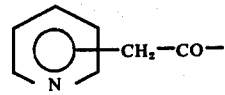

group, a —CO-pyridyl group, and a —CO-$R_3$ group, wherein $R_3$ represents the residue of any N,N-$C_1$-$C_2$—dialkylamino acid or a $C_4$-$C_6$ cycloalkylamino acid; wherein $R_1$ represents a member selected from the group consisting of a hydroxyl group and a -OM group, wherein M is defined as above; and wherein $R_2$ represents a member selected from the group consisting of a

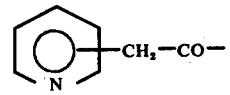

group, a -CO-pyridyl group, and the —CO-$R_3$ group, wherein $R_3$ represents the residue of any N,N—$C_1$—$C_2$-dialkylamino acid or a 5- or a 6 membered N-cycloalkylamino acid. Illustrative of said dialkylamino acids and N-cycloalkylamino acids are:
 1. N,N-dimethylaminoglycine
 2. N,N-diethylaminoglycine
 3. 1-piperidine acetic acid
 4. 1-pyrrolidine acetic acid

THE COMPOUNDS OF CLASS (II)

These compounds constitute the N-terminal dipeptides of the catechol acylated L-DOPA, wherein R represents an acyl group; wherein $R_2$ represents a hydrogen atom; and wherein $R_1$ represents a —NHCH($R_4$)COO$R_5$ group, wherein $R_4$ represents the residue of any naturally occurring amino acid, and wherein $R_5$ represents a member selected from the group consisting of a hydrogen atom, a $C_1$-$C_5$ alkyl group (e.g., methyl, ethyl, propyl, butyl, etc.), and a $C_1$-$C_5$ alkylaryl group (e.g., benzyl, phenylethyl, phenylpropyl, 1,2 or 3-methylbenzyl, ethylbenzyl, propylbenzyl, etc.), and the HX salts thereof, wherein X is defined as above.

THE COMPOUNDS OF CLASS (III)

The compounds of this class constitute the C-terminal dipeptides of the catechol acylated L-DOPA, wherein R represents an acyl group; wherein $R_1$ represents a member selected from the group consisting of a hydroxyl group, a —OCH$_3$ group, a —OC$_2$H$_5$ group, a —OC$_3$H$_7$ group, a —OC$_4$H$_9$ group, and a —OCH$_2$-C$_6$H$_5$ group; and wherein $R_2$ represents an NH$_2$CH($R_6$)CO— group, wherein $R_6$ represents the residue of a naturally occurring amino acid, and the HX salts thereof, wherein X is defined as above.

THE COMPOUNDS OF CLASS (IV)

The compounds of this class are those compounds of Class (III) which are basically dipeptides formed from two molecules of 3,4-diacyloxy-L-phenylalanine, wherein R represents a member selected from the group consisting of an acyl group; wherein $R_1$ represents a member selected from the group consisting of a hydroxyl group, a $-OCH_3$ group, a $-OC_2H_5$ group, a $-OC_3H_7$ group, a $C_4H_9$ group, and a $-OCH_2\text{-}C_6H_5$ group; and wherein $R_2$ represents an $NH_2\text{-}CH(R_7)-CO-$ group, wherein $R_7$ represents the residue of a 3,4-L-diacyloxyphenylalanine group of the formula:

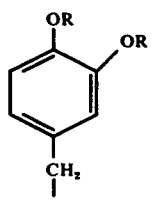

wherein R is defined as above, and HX salts thereof, wherein X is defined as above.

THE COMPOUNDS OF CLASS (V)

The compounds of this class are those compounds encompassed within formulas (V-A) and (V-B), respectively, set out below:

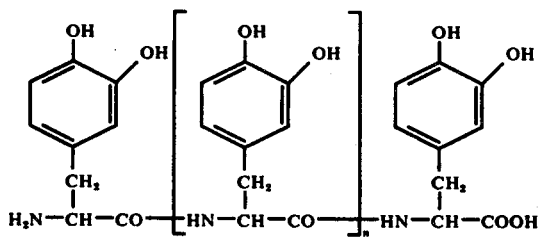

(V-A)

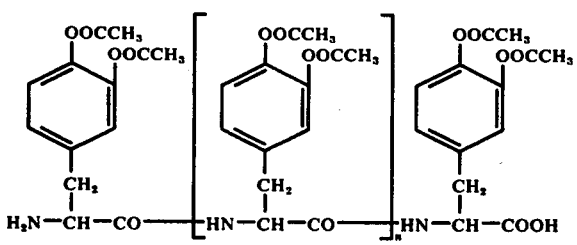

(V-B)

wherein $n$ represents an integer of 2–50 for formula (V-A) and represents an integer of 1–50 for formula (V-B). Preferably, however, in either case, $n$ should be within a range of from seven (7) to twenty (20).

This class basically constitutes the polypeptides of L-DOPA, per se, or its 3,4-diacetylated derivatives.

The compounds of classes (I) through (V) can be prepared by simple step-wise procedures as outlined below and as described in the various publications recited.

PREPARATION OF THE COMPOUNDS OF CLASS (I)

These compounds are prepared by reacting L-DOPA with conventional acylating agents, such as acyl chloride or acyl anhydride, or in the alternative, a conventional "mixed anhydride" system can be used. The reaction is carried out in a suitable solvent, such as an organic acid (e.g., acetic acid, propionic acid, etc.) at room temperature and standard pressure. In the alternative, the reaction can be carried out effectively in a halohydrocarbon solvent at reflux temperatures in the presence of a tertiary amine. In either case, the reaction is carried out for a period ranging from 1 to 6 hours. See, J. C. Sheehan and D. D. H. Yang, *J. Amer. Chem. Soc.*, 80, 1154 (1958).

PREPARATION OF THE COMPOUNDS OF CLASS (III)

The preparation of the compounds of this class is discussed prior to the preparation of the compounds of class (II) as a matter of convenience.

The preparation of the compounds of class (III) is carried out in accordance with conventional dipeptide synthesis procedures. In the first step, acylation of the catechol hydroxyl groups is carried out in accordance with the acylation procedure described above relative to the preparation of the compounds of class (I). Secondly, the carboxyl group of the diacylated L-DOPA is esterified in accordance with the esterification procedure outlined for the preparation of the compounds of class (I), as well. In the third step, the protected L-DOPA molecule is coupled with a suitable N-protected natural amino acid by known procedures (e.g., dicyclohexylcarbodiimide in tetrahydrofuran and/or a halohydrocarbon). This reaction is carried out at room temperature over a period of time ranging from 3 to 24 hours; however, as an alternative, the "mixed anhydride" method can be employed at a temperature of 0° C initially (for 0.5 to 1.0 hours) and then, at a temperature approximating room temperature for a period of time ranging from 3 to 6 hours. The "mixed anhydride" can, without limitation be formed from pivalyl chloride, t-butyl chloroformate, or iso-butyl chloroformate.

At this point, it is important to mention that steps (1) through (3) heretofore described need not necessarily be carried out in sequential order; that is, the sequence can vary with the proviso that steps (1) or (2) must proceed step (3).

Illustrative of N-protective groups for the amino acid which can be employed in step (3) are the carbobenzoxy group and the formyl group.

In step (4), cleavage of the N-protective group is achieved in a conventional manner. As an example, when the N-protective group is a carbobenzoxy group, catalytic hydrogenation is employed over a catalyst comprising palladium on carbon (5–10%) in methanol or ethanol or any other suitable solvent. The reaction is carried out at standard pressure, room temperature, and for a period of time approximating several hours. When the N-protective group is a formyl group, its cleavage can be carried out by using various procedures, and preferentially, in a mixture of methanol and hydrochloric acid. The reaction is normally carried out at standard pressure and room temperature over a period of time ranging from 4 to 24 hours.

In step (5), cleavage of the carboxy ester ($R_1$), if required, is achieved. For instance, if $R_1$ is a $-CH_2\text{-}$ $C_6H_5$ group, catalytic hydrogenation is carried out over a catalyst of palladium on carbon (5–10%) in methanol or ethanol, at standard pressure and room temperature. On the other hand, if $R_1$ represents a —$OCH_3$ group, alkaline hydrolysis is employed (sodium hydroxide, sodium bicarbonate, barium hydroxide, etc.) in the presence of alcohol, methanol or ethanol under a nitrogen atmosphere, at room temperature, and for a period of time approximating several hours.

Finally, in step (6), adjustments to the isolated L-DOPA derivative can be made, such as salt formation (if the reaction did not directly provide the salt) and reacylation of the catechol system if the acyl groups are cleaved off in the previous steps. Such procedures are known and understood by the skilled artisan concerned with the subject matter of this invention.

PREPARATION OF THE COMPOUNDS OF CLASS (II)

These compounds are prepared in a manner similar to that employed to prepare the compounds of class (III). Step (1) of this procedure is identical to step (1) of the procedure employed to prepare the compounds of class (III). In step (2), protection of the amino group is achieved through the use of conventional protective groups, and preferably, the formyl group. For instance, the N-formyl derivative can be prepared by the "mixed" acetic-formic anhydride method, in acetic acid, by first cooling the reaction mixture below room temperature and then raising the temperature of the reaction mixture to room temperature for approximately 1 hour. In step (3), coupling with a suitable natural amino acid ester is carried out in the manner described in step (3) for the preparatory procedure described for preparing the compounds of class (III). In step (4), cleavage of the carboxy ester, if required, is achieved. For instance, if the carboxy ester is a benzyl ester, catalytic hydrogenation is carried out over a palladium on carbon (5–10%) catalyst as illustrated in step (4) respective of the preparatory procedure for preparing the compounds of class (III). On the other hand, if the carboxy ester is a methyl or ethyl ester, alkaline hydrolysis is employed in accordance with the method described in step (5) of the preparatory scheme for preparing the compounds of class (III). In step (5), cleavage of the N-protective group is carried out in accordance with step (4) of the preparatory procedure for obtaining the compounds of class (III), the procedure varying depending upon whether the N-protective group is a carbobenzoxy group, a formyl group, or any other suitable protective group. Step (6) is identical to step (6) described above in the preparatory scheme for preparing the compounds of class (III).

The skilled artisan concerned with the subject matter of this invention can readily appreciate that steps (4) and (5) can occur simultaneously in accordance with the above recited conditions. Moreover, with respect to the preparation of the compounds of class (III), in addition to the fact that steps (1) and (2) can be varied in sequence, provided they precede step (3), steps (4) and (5) can also be varied with the proviso that they follow step (3).

Few dipeptides containing C- or N-terminal D, L-DOPA have been reported in the literature, such as D, L-3,4-dihydroxyphenylalanylglycine, -D, L-alanine, -D, L-leucine, -D, L-phenylalanine, -D, L-tyrosine, using phthaloyl-D, L-3,4-dihydroxyphenylalanine, since it was concluded that the amino group in D, L-DOPA cannot be protected with carbobenzoxy or p-nitrocarbobenzoxy groups. The phthaloyl protecting group, however, cannot be used for the protection of the amino group in L-DOPA, since applicants have observed extensive racemization during the preparation of the phthaloyl-L-DOPA. Some C-terminal D, L-DOPA dipeptides have been reported by coupling D, L-DOPA-methyl ester and some simple N-carbenzoxy amino acids. See, G. Losse, A. Barth and K. Jasche, J. Prakt. Chem., 21, 32 (1963), and G. Losse, A. Barth and W. Langenbeck, Chem. Ber., 95, 918 (1962), respectively.

The methyl ester could be hydrolyzed under $N_2$ after the N-carbobenzoxy group was cleaved. The phthalylglycyl-D, L-3,4-dihydroxyphenylalanine-methyl ester was also reported, but the protective groups were not cleaved. See, J. J. O'Neill, F. P. Veitch and T. Wagner-Jauregg, J. Org. Chem., 21, 363 (1956).

In one instance, the preparation of β-alanyl-L-3,4-dihydroxy-phenylalanine was reported. However, the way it was prepared, as well as the insufficient characterization of the dipeptide leads one to believe that it is highly unlikely that the compound was actually obtained at all. See, C. Pinelli, M. Portelli, and M. Fioretti, Farmaco (Ed. Sci.), 23, 859 (1968).

A. V. Bardoshian, et al., Anal. Biochem., 49, 569 (1972) reported the use of L-leucyl-L-3,4-dihydroxyphenylalanine, which was used for the separation on TLC of the optical isomers of labeled DOPA.

In view of the above available literature data, applicants decided to use the N-formyl-diacetyl-L-DOPA for the preparation of the N-terminal dipeptides and the diacetyl-L-DOPA-benzyl ester for the preparation of the C-terminal dipeptides. DCC (dicyclohexyl-carbodiimide) was used as the coupling agent in all cases.

The N-formyl group can be cleaved with diluted hydrochloric acid in alcohol, by catalytic hydrogenation or by oxidation with $H_2O_2$ and the benzyl esters and the N-carbobenzoxy groups can be removed via catalytic hydrogenation. See, G. Losse, and D. Nadolski, J. Prakt. Chem., 24, 118 (1964), and G. Losse and W. Zonnchen, Ann., 636, 140 (1960).

PREPARATION OF THE COMPOUNDS OF CLASSES (IV) and (V)

The compounds of class (IV) are prepared in a manner similar to that described for the preparation of the dipeptides of classes (II) and (III). As the starting materials, we have on the one hand, 3,4-diacylated, N-protected L-DOPA, and on the other hand, we have the carboxy esters of 3,4-diacylated L-DOPA. Thus, N-formyl-3,4-diacetyloxy-L-phenylalanine was coupled with 3,4-diacetyloxy-L-phenylalanine-methyl ester. By treatment with methanolic HCl, the N-formyl and acetyloxy groups were cleaved, thus obtaining 3,4-dihydroxy-L-phenylalanyl-3,4-dihydroxy-L-phenylalanine-methyl ester HCl. The free dipeptide was obtained by alkaline hydrolysis of the methyl ester in an inert atmosphere.

In the next step, the corresponding bis-3,4-diacetylated dipeptide was obtained by acylation of the free dipeptide, using the acylation scheme described in acylating the ester compounds of class (I) above.

The compounds of class (V) are obtained, using general procedures as outlined in the literature reference by Greenstein and Winitz, "The Chemistry of Amino Acids and Peptides," Volume 2 (1964), published by McGraw-Hill with the proviso that the hydroxyl groups of the catechol system must be protected through acylation prior to preparing a polypeptide. Accordingly, 3,4-diacetyloxy-L-phenylalanoyl chloride HCl can be obtained by treatment of 3,4-diacetyloxy-L-phenylalanine with PCl$_5$ in acetyl chloride. The obtained chloride, after neutralization, undergoes coupling to form the corresponding acylated polypeptide.

The acetyl groups can be removed via alkaline or acid hydrolysis to form the free polypeptide. This reaction is carried out at standard pressure and at a temperature of about 0° C over a period of time ranging from 1 to 4 hours.

The compounds of the present invention are administered orally in the form of any oral, pharmaceutically acceptable dosage form (capsule, tablet, and the like). Generally speaking, the dosage amount of the compound administered, on a daily basis, will vary with the needs of the individual treated. However, normally, the dosage regimen will mimic that of L-DOPA, per se.

Without further elaboration, it is believed that one of ordinary skill in the art can, using the preceding description, utilize the instant invention to its utmost extent. The following preferred specific embodiments are, therefore, to be construed as merely illustrative, and not limitative, of the remainder of the specification and claims in any way whatsoever.

EXAMPLE I (Preparation of 3,4-diacetyloxy-L-phenylalanine hydrochloride)

L-DOPA (19.72 g, 0.01 mole) is dissolved as its hydrochloride salt in 500 ml of glacial acetic acid by heating the same to approximately 100° C and adding HCl gas. The resulting clear solution is permitted to cool to 45° C and then 71 ml (78.5 g, 1.0 mole) of acetyl chloride is added slowly to the above-described solution. The reaction mixture is stirred at room temperature for approximately 16.0 hours using a drying tube filled with calcium chloride to protect it from atmospheric moisture. The entire reaction mixture is then added to one liter of ether and stirred for 15 minutes and the resulting product is recovered by filtration.

The yield of final product was 28.5 g (90%). The melting point of the final product was 192°–193° C (uncorrected). The nuclear magnetic resonance spectrum (nmr) was consistent with the compound obtained. The Analysis Calculated for: $C_{13}H_{16}O_6NCl$ was: C, 49.14; H, 5.08; N, 4.41; and Cl, 11.16. Found: C, 48.98; H, 5.26; N, 4.17; and Cl, 11.25.

EXAMPLE II (Preparation of 3,4-dihydroxy-L-phenylalanine-methyl ester hydrochloride and 3,4-diacetyloxy-L-phenylalanine-methyl ester hydrochloride)

First, 3,4-dihydroxy-L-phenylalanine-methyl ester hydrochloride was prepared. To obtain this compound, thionyl chloride (10.16 ml) was added, drop-wise to a cool (ice-bath) well-stirred absolute methanol (101.6 ml). To this solution, there was then added 23.02 g (0.117 mole) of 3,4-dihydroxy-L-phenylalanine, in portions, such that the temperature was maintained at 5° C. The solution was kept at 40° C for 2.5 hours and then, the solution was concentrated, in vacuo to dryness. Dry ether was added to the residue and the solution was cooled overnight to yield 28.67 g (mp 169°–172° C) of final product, a 99.3% yield. The nmr spectrum was consistent with the proposed structure for the compound obtained and analysis of the final compound obtained was as follows: Analysis Calculated for: $C_{10}H_{14}NO_4Cl$: C, 48.48; H, 5.70; and N, 5.66. Found: C, 47.95; H, 5.30; and N, 6.16.

In the next step, the obtained 3,4-dihydroxy-L-phenylalanine-methyl ester hydrochloride was then acylated in the following manner. A glacial acetic acid (661 ml) suspension containing 25.4 g (0.1 mole) of 3,4-dihydroxy-L-phenylalanine-methyl ester hyrochloride was warmed to 110° C and subsequently, hydrogen chloride was bubbled through the mixture for a period of 4 minutes. The solution was cooled to 45° C and acetyl chloride (101.3 ml) was then added. This solution was stirred at room temperature overnight and then diluted with 1.5 liters of dry ether. White crystals began to precipitate immediately and, subsequently, these crystals were filtered and dried over phosphorous pentoxide to yield 28.51 g (mp 181°–183° C, 83.7% yield) of the final product. The nmr spectrum was consistent with 3,4-diacetyloxy-L-phenylalanine-methyl ester hydrochloride. Upon analysis, the following data was obtained. Analysis Calculated for: $C_{14}H_{18}NO_4Cl$: C, 50.68; H, 5.47; N, 4.22; and Cl, 10.70. Found: C, 50.50; H, 5.21; and N, 4.67.

A sample of the obtained 3,4-diacetyloxy-L-phenylalanine-methyl ester hydrochloride was recrystallized from methanol-ether to yield the analytically pure compound. Found: C, 50.42; H, 5.61; N, 4.09; and Cl, 10.44.

In a similar manner described above, the compound 3,4-diacetyloxy-L-phenylalanine benzyl ester hydrochloride can be prepared and was prepared. Upon analysis, the following data was obtained. Analysis Calculated for: $C_{20}H_{22}O_6NCl$: C, 58.89; H, 5.44; N, 3.44; and Cl, 8.69. Found: C, 58.58; H, 5.48; N, 3.33; and Cl, 8.95.

EXAMPLE III (Preparation of 3,4-dihydroxy-L-phenylalanine-benzyl ester hydrochloride)

3,4-dihydroxy-L-phenylalanine (15.0 g, 0.076 mole) was suspended in benzyl alcohol (381 ml). This suspension was then cooled with an ice bath to 5° C and then the suspension was treated with thionyl chloride (76.2 ml). The resulting solution was heated to within a temperature range of from 95° to 100° C for 5.0 hours in a nitrogen atmosphere and then the suspension was cooled to room temperature and diluted with 1.5 liters of dry ether to yield a solid precipitate. The suspension was stirred at room temperature overnight, filtered, and then washed with ether and dried in a vacuum oven to yield 7.70 g (32% yield) of the desired benzyl ester hydrochloride having a mp of 171°–175° C, with shrinking at 165° C.

An oil had also formed in the bottom of the reaction flask overnight and this oil was dissolved in a minimal amount of methanol. A white solid was precipitated with ether, and the white solid was filtered and then dried in a vacuum oven to give 1.20 g (5% yield, mp 178°–181° C) of the benzyl ester hydrochloride. The nmr spectrum was consistent with the proposed structure of the compound isolated and upon analysis the following data was obtained. Analysis Calculated for: $C_{16}H_{18}NO_4Cl$: C, 59.35; H, 5.60; and N, 4.33. Found: C, 59.47; H, 5.32; and N, 4.76. The nmr spectrum of the fraction was identical with that of the analytical sample.

EXAMPLE IV (Preparation of glycyl-3,4-diacetyloxy-L-phenylalanine hydrochloride)

First, carbobenzoxyglycyl-3,4-diacetyloxy-L-phenylalanine-benzyl ester was obtained in the manner which follows. Dichloromethane (100 ml) solution containing 0.95 g (9.4 millimole) of triethylamine was permitted to react with 3.64 g (8.92 millimole) of 3,4-diacetyloxy-L-phenylalanine-benzyl ester hydrochloride for 0.3 hours at room temperature. The solution was then concentrated in vacuo at room temperature to dryness. The residue obtained was filtered and washed with ether to give 1.54 g of triethylamine hydrochloride, contaminated with 3,4-diacetyloxy-L-phenylalanine-benzyl ester in various stages of deprotection. For instance, 3,4-dihydroxy-L-phenylalanine-benzyl ester was obtained quantitatively if a large excess of triethylamine was employed to neutralize the hydrochloride. The ether filtrate was concentrated in vacuo at room temperature. The resulting residue was analyzed by nmr and found to be consistent with the proposed structure, 3,4-diacetyloxy-L-phenylalanine-benzyl ester.

The residue was estimated to contain 8.15 millimole of 3,4-diacetyloxy-L-phenylalanine-benzyl ester. The residue was dissolved in dichloromethane (50 ml) and carbobenzoxyglycine (1.70 g, 8.16 millimole) and dicyclohexylcarbodiimide (1.68 g, 8.15 millimole) was added to the solution in the order given. A white precipitate of dicyclohexylurea (DCCU) began to form immediately. The following day, the suspension was filtered and the residue was washed with dichloromethane (50 ml) to yield 1.55 g (85% yield) of DCCU. The combined dichloromethane filtrates were washed with 10 ml each, of 1N hydrochloric acid and water and then concentrated in vacuo at room temperature to give 4.6 g of an oily residue. The oily residue was chromatographed on silica gel (Mallinckrodt Silic ARCC-7) using ether as the eluent to give 2.70 g of a yellow oil (1 spot on TLC, Rf 0.63 on silica gel, acetone eluent) whose nmr spectrum was consistent with carbobenzoxyglycyl-3,4-diacetyloxy-L-phenylalanine-benzyl ester, but which contained some impurities from the ether eluent. The oil was dissolved in ether (100 ml) and diluted with heptane. The ether-heptane mixture was decanted from the oil which formed. The oil (2.00 g, 44% yield) gave an nmr spectrum consistent with the carbobenzoxyglycyl-3,4-diacetyloxy-L-phenylalanine-benzyl ester. The oil would not crystallize and was therefore employed without further purification in the next reaction step.

In this step, glycyl-3,4-diacetyloxy-L-phenylalanine hydrochloride was obtained as follows. 2.48 g (4.4 millimole) of carbobenzoxyglycyl-3,4-diacetyloxy-L-phenylalanine-benzyl ester was dissolved in 120 ml of methanol with 5 ml of glacial acetic acid. Then, 0.5 g of 10% Pd/C (palladium on carbon) was wetted with water (5 ml) and washed into the solution with water (approximately 5 ml). The resulting suspension was shaken in hydrogen (30 lbs) for 24 hours. The suspension was filtered and washed with methanol (100 ml) and the combined filtrates were concentrated in vacuo at room temperature. The residue was dissolved in 10 ml of glacial acetic acid, saturated with hydrogen chloride and then treated with 10 ml of acetyl chloride in a tightly stoppered flask overnight and subsequently the solution was diluted to 125 ml with ether. After two hours, the ether was decanted and the gummy residue obtained was suspended in dry ether and left stirring overnight. Then, the suspension was quickly filtered and the residue was dried in vacuo at 60° C to yield 0.87 g (mp 95°–118° C) of the glycyl-3,4-diacetyloxy-L-phenylalanine hydrochloride. Analysis Calculated for: $C_{15}H_{19}N_2O_7Cl$: C, 48.06; H, 5.11; and N, 7.48. Found: C, 48.42; H, 5.38; and N, 7.30.

EXAMPLE V (Preparation of glycyl-3,4-diacetyloxy-L-phenyl-alanine-methyl ester hydrochloride)

A dichloromethane solution (150 ml) of 3,4-diacetyloxy-L-phenylalanine-methyl ester hydrochloride (4.316 g, 13.0 millimole) was permitted to react with 1.35 g (13.3 millimole) of triethylamine. After 10 minutes, 2.718 g (13.0 millimole) of carbobenzyloxyglycine was added thereto, and then 2.808 g (13.6 millimole) of dicyclohexylcarbodiimide was added. After 2 hours, the solution was filtered to yield 2.62 g (mp 228°–230° C, 90% yield) of DCCU. The filtrate was extracted with 10 ml each of 1N HCl and water. The dichloromethane layer was dried over sodium sulfate and concentrated in vacuo at room temperature to give 16.5 g of a white solid (1 spot of TLC Silica gel, acetone, Rf 0.42). The white solid was dissolved in dichloromethane (60 ml) and the solution was then filtered and diluted to 220 ml with hexane. The following day the solution was filtered and the residue was air dried to give 5.5 g (mp 130°–131° C, 87% yield) of carbobenzyloxyglycyl-3,4-diacetyloxy-L-phenylalanine-methyl ester. The mother liquor was concentrated (45 ml) to give 233 mg (mp 129°–130° C, 3% yield) more of the aforementioned ester. The nmr spectrum was consistent with the proposed structure of the compound isolated.

Upon analysis, the following data was obtained. Analysis Calculated for: $C_{24}H_{26}N_2O_9$: C, 59.25; H, 5.39; and N, 5.76. Found: C, 59.54; H, 5.39; and N, 5.74.

Next, 3.00 g (6.17 millimole) of the above isolated ester was dissolved in methanol (100 ml) and glacial acetic acid (5 ml). The solution was then shaken in a Parr apparatus for 16 hours over 10% Pd/C (0.4 g) under a hydrogen atmosphere (35 lbs). The solution was then filtered and concentrated in vacuo at room temperature. The residue obtained was dissolved in 10 ml of glacial acetic acid, saturated with hydrogen chloride and treated with 10 ml of acetyl chloride. The solution was stirred at room temperature overnight in a tightly sealed reaction flask and then diluted to 125 ml with ether to give a light brown gum. The ether was decanted and the residue was suspended in anhydrous ether (100 ml). The suspended solid was dispersed with a spatula and allowed to stir until it became homogeneous. It was then filtered and the residue was dried in a vacuum oven at 60° C to yield 0.58 g (mp 80°–100° C, 24% yield) of glycyl-3,4-diacetyloxy-L-phenylalanine-methyl ester hydrochloride from carbobenzyloxyglycyl-3,4-diacetyloxy-L-phenylalanine-methyl ester. The nmr spectrum was consistent with the proposed structure of the compound obtained and upon analysis of the compound, the following data was obtained. Analysis Calculated for: $C_{16}H_{21}O_7N_2Cl$: C, 49.42; H, 5.44; and N, 7.21. Found: C, 49.65; H, 5.50; and N, 7.47.

EXAMPLE VI (Preparation of 3,4-diacetyloxy-L-phenylalanyl-glycine hydrochloride)

First, it was necessary to prepare 3,4-diacetyloxy-L-phenylalanine-N-formate. This product was obtained in the manner described below.

3,4-diacetyloxy-L-phenylalanine hydrochloride (15.00 g, 47.2 millimole) was dissolved in 20 ml of methanol and diluted to 900 ml with dichloromethane. To this solution, there was added, with vigorous stirring, 4.80 g (47.5 millimole) of triethylamine, which caused a gelatinous mass to form. After one hour, this mass was filtered and the residue was suspended in dichloromethane (300 ml) and filtered again. The residue was still contaminated with triethylamine hydrochloride. Consequently, it was suspended in dichloromethane (300 ml) again, and stirred for 3.5 hours. The suspension was filtered and dried a room temperature in vacuo to yield 12.5 g (95% yield by nmr) of 3,4-diacetyloxy-L-phenylalanine.

Next, 12.5 g (44.6 millimole) of the isolated 3,4-diacetyloxy-L-phenylalanine was dissolved in 35 ml of 98% formic acid and cooled with an ice bath at 5° C. Acetic anhydride (9.6 g, 94.1 millimoles) was added, drop-wise to the cool, well-stirred solution in such a manner that the temperature remained at 5° C. After 3 hours, the solution was concentrated in vacuo at room temperature and the residue was dissolved in acetone (200 ml). This process was repeated twice and the residue was recrystallized from acetone, (750 ml) to yield 4.95 g (mp 135°–137° C) of 3,4-diacetyloxy-L-phenylalanine-N-formate. The mother liquor was concentrated on a hot plate to 40 ml and then cooled to yield 3.50 g (mp 130°–135° C) of 3,4-diacetyloxy-L-phenylalanine-N-formate. The mother liquor was again concentrated to yield 1.75 g (mp 123°–133° C) of the aforementioned compound, after which the solution was diluted with 200 ml of ether to yield 1.53 g (mp 112°–120° C) of 3,4-diacetyloxy-L-phenylalanine-N-formate. All fractions had the same TLC (Rd 0.5 silica gel, acetone). The last two fractions were combined and recrystallized from acetone (20 ml) to yield 1.50 g (mp 130°–135° C) of 3,4-diacetyloxy-L-N-formate for a 69% yield (9.95 g) of the pure compound. The nmr spectrum was consistent with the proposed structure of the compound obtained.

Next, N-formyl-3,4-diacetyloxy-L-phenylalanyl-glycine-benzyl ester was prepared. To obtain this compound, the 3,4-diacetyloxy-L-phenylalanine-N-formate, obtained earlier (4.015 g, 13.00 millimole) was added to a dichloromethane (200 ml) solution, containing triethylamine (1.35g, 13.3 millimole) and glycine benzyl ester p-toluenesulfonate (4.40 g, 13.06 millimole). The resulting suspension was vigorously shaken until all of the 3,4-diacetyloxy-L-phenylalanine-N-formate was in solution. Then, 2.80 g (13.6 millimole) of dicyclohexylcarbodiimide was added. After 4.5 hours, the reaction was filtered and the residue (2.41 g, mp 206°–210° C, 83% yield) of DCCU was discarded. The filtrate was extracted with 10 ml each of water and 1N HCl. The dichloromethane solution was then dried over sodium sulfate and concentrated in vacuo at room temperature. The residue was chromatographed on silica gel (Silic ARCC-7) using acetone-ether (20:80 to 40:60) as the eluent to give 2.33 g (39% yield) of N-formyl-3,4-diacetyloxy-L-phenylalanyl-glycine-benzyl ester (mp 120.5°–120° C). The nmr spectrum was consistent with the proposed structure of the compound isolated. Upon analysis the following data was obtained. Analysis Calculated for: $C_{23}H_{24}N_2O_8$: C, 60.52; H, 5.29; and N, 6.14. Found: C, 60.25; H, 5.10; and N, 6.01.

Next, the step of deprotecting the N-formyl-3,4-diacetyloxy-L-phenylalanyl-glycine-benzyl ester was performed. 0.90 g (2.0 millimole) of the aforementioned compound was allowed to react with a 2.2 ml of a 1N methanolic-hydrochloric acid solution (prepared by diluting 2 ml of concentrated hydrochloric acid to 24 ml with methanol) overnight. Initially, a suspension formed and an additional 5 ml of methanol was added to the suspension. After about 0.5 hours, all of the solid had gone into solution. The solution was concentrated in vacuo at room temperature and the nmr spectrum of the residue showed the absence of $CH_3CO_2$ and O=CH-N absorptions. The residue was dissolved in 60 ml of anhydrous methanol to which 0.5 ml of glacial acetic acid had been added. The solution was shaken in a Parr shaker under hydrogen atmosphere over 0.1 g of a 10% Pd/C catalyst overnight. The suspension was then filtered to remove the catalyst and concentrated in vacuo at room temperature. The residue was twice diluted with acetone (100 ml) and concentrated. Then, it was dissolved in glacial acetic acid saturated with hydrogen chloride (10 ml) and allowed to react with acetyl chloride (10 ml). A solid formed, but soon went back into solution. After eight hours at room temperature, the acetic acid solution was then diluted to 125 ml with ether. The ether was then decanted and the gummy dark residue left behind was suspended in ether (100 ml). The suspension was stirred overnight to yield a fine white solid in suspension, which was filtered quickly and dried in vacuum desiccator to yield 0.59 g (shrinking at 100° C, wet at 114° C, and foaming from 120°–127° C, 78% yield) of 3,4-diacetyloxy-L-phenylalanyl-glycine hydrochloride. The nmr was consistent with the proposed structure of the compound obtained and upon analysis of a sample of this compound, by recrystallization from methanol-ether, the following data was obtained. Analysis Calculated for: $C_{15}H_{19}N_2O_7Cl$: C, 48.06; H, 5.11; and N, 7.48. Found: C, 48.22; H, 5.34; and N, 7.72.

The preceding examples can be repeated with similar success by merely substituting the generically or specifically described reactants and/or operating conditions of this invention for those of the preceding examples.

IN VIVO COMPARISON OF L-DOPA PER SE VERSUS SELECTIVE L-DOPA DERIVATIVES OF THE PRESENT INVENTION

In Table I, reproduced on the following page, values are shown relative to the blood concentration of L-DOPA per se and selected L-DOPA derivatives of the present invention, following oral administration of 0.1 of L-DOPA and an equivalent amount of an L-DOPA derivative of this invention to Beagle dogs.

TABLE I

| Compound No. | [L-DOPA] (μg/ml) at time (hours) (a) | | | | | | | μg/hr/ml area under the curve | μg./ml L-DOPA at the peak | hours time for reaching the peak |
| --- | --- | --- | --- | --- | --- | --- | --- | --- | --- | --- |
| | 0.5 | 1.0 | 1.5 | 2.0 | 3.0 | 4.0 | 6.0 | | | |
| (0) | 0.14 | 0.64 | — | 0.87 | — | 0.22 | 0.11 | 2.6 | 0.9 | 1.8 |
| (I) | 0.06 | 1.13 | 1.11 | 0.39 | 0.12 | 0.09 | 0.02 | 3.56 | 1.6 | 1.2 |
| (II) | 1.71 | 1.30 | 1.08 | 0.55 | 0.20 | 0.14 | 0.05 | 5.96 | 2.3 | 0.5 |
| (III) | 1.34 | 1.95 | 1.21 | 0.43 | 0.27 | 0.13 | 0.02 | 7.25 | 2.4 | 0.75 |
| (IV) | 0.79 | 1.17 | 0.51 | 0.33 | 0.08 | 0.02 | 0 | 3.38 | 1.7 | 0.80 |
| (V) | 0.26 | 1.30 | 1.62 | 0.80 | 0.23 | 0.03 | 0 | 5.30 | 1.8 | 1.2 |

Respective of Table I, the following information is pertinent:

Reference to (a) refers to the values obtained from three Beagle dogs for each compound tested, the Beagle dogs being of both sexes and weighing from 12 to 14 Kg.

Reference to [L-DOPA] refers to the concentration of L-DOPA

Compound(O) is L-DOPA per se.

Compound (I) is 3,4-diacetyloxy-L-phenylalanine-methyl ester, HCl.

Compound (II) is 3,4-diacetyloxy-L-phenylalanine-benzyl ester hydrochloride.

Compound (III) is glycyl-3,4-diacetyloxy-L-phenylalanine-hydrochloride.

Compound (IV) is glycyl-3,4-diacetyloxy-L-phenylalanine-methyl ester hydrochloride.

Compound (V) is 3,4-diacetyloxy-L-phenylalanyl-glycine hydrochloride.

The blood level data provided above in Table I was obtained according to the published procedures set forth in Items (1) through (9).

1. H. E. Spiegel and A. C. Tonchen, Clinical Chemistry, Volume 16, No. 9 (1970).
2. T. L. Soures and G. S. Murphy, Methods Med. Res., 9, 147 (1961).
3. H. Takashi and T. B. Fitzpatrick, J. Invest. Dermatol., 41, 161 (1964).
4. A. Carlson and D. Waldeck, A. C. T. A. Physiol. Scandinav., 44, 293 (1958).
5. R. Bruce, Anal. Chem., 41. 977 (1969).
7. E. Anggard, Ibid, 41, 1250 (1969).
8. E. Anggard, A. C. T. A. Chim. Scand., 23, 3110 (1969).
9. S. T-ahn, A. L. Prasad, R. Eelesie, Analyt. Biochemistry, 46, 557 (1972).

The above results clearly demonstrate that the L-DOPA prodrug forms of this invention permit L-DOPA to be releaed in the bloodstream at higher blood levels than that level achieved with L-DOPA per se. This indicates that the various pro-drugs studied, provide efficient protection of the L-DOPA molecule against extensive metabolism prior and/or during the adsorption process. Moreoever, the above studies demonstrate that the two pro-drugs were converted back to L-DOPA in accordance withthe "pro-drug" definition provided at the outset of this application.

The pro-drug forms of this invention are suitably administered in oral dosage form, such as by tablet or capsule, by combining the same in a therapeutic amount with any oral pharmaceutically acceptable inert carrier, such as lactose, starch (pharmaceutical grade), dicalcium phosphate, calcium sulfate, kaolin, mannitol, and powdered sugar. In addition, when required, suitable binders, lubricants, disintegrating agents, and coloring agents can also be added to the oral dosage form. Typical binders include starch, gelatin, sugars, such as sucrose, molasses, and lactose, natural and synthetic gums, such as acacia, sodium alginate, extract of Irish moss, crboxymethylcellulose, methyl cellulose, and polyvinylpyrrolidone, polyethylene glycol, ethylcellulose, and waxes. Typical lubricants for use in these dosage forms can include, without limitation, boric acid, sodium benzoate, sodium acetate, sodium chloride, leucine, and polyethylene glycol. Suitable disintegrators can include without limitation, starch, methylcellulose, agar, bentonite, cellulose and wood products, alginic acid, guar gum, citrus pulp, carboxymethylcellulose, and sodium lauryl sulfate. If desired, a conventionally pharmaceutically acceptable dye can be incorporated into the dosage unit form.

Any skilled artisan can prepare these oral dosage forms by simply referring to the oral dosage form preparatory procedure outlined in Remington's Practice of Pharmacy, Fourteenth Edition, (1970), pages 1659 througgh 1698, inclusive.

While the therapeutic dosage range for the compounds of this invention will vary with the needs of the individual, generally speaking therapeusis on a daily basis is achieved with about 1/3 the amount of the L-DOPA therapeutic dosage amount administered at present. In certain cases, therapeusis is achieved with less than 1/3 the amount of the normal L-DOPA therapeutic dosage amount. These dosage guidelines are independent of the patient's size and/or weight.

As an example, an adult human male, suffering from Parkinson's Disease can be successfully treated by administering, on a daily basis, about 2.0 grams of the L-DOPA pro-drug form of Compound (III) described at page 32 (glycyl-3,4-diacetyloxy-L-phenylalanine-hydrochloride).

Although the present invention has been adequately described in the foregoing specification and examples included therein, it is obviously apparent that various changes and/or modifications can be made thereto by the skilled artisan without departing from the spirit and scope thereof. Consequently, such changes and/or modifications are properly, equitably and intended to be, within the full range of equivalence of the following claims.

What we claim is:

1. A method for treating Parkinson's Disease in warm-blooded animals which comprises orally administering to a warm-blooded animal afflicted with Parkinson's Disease, an anti-Parkinsonism effective amount of a compound having the formula:

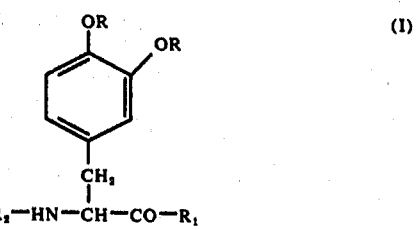

wherein R represents a hydrogen atom, an acyl group and a —CO—R₃ group, wherein R₃ represents the residue of any N,N-C₁-C₂ dialkylamino acid or a C₄-C₆ cycloalkylamino acid; wherein R₁ represents a member selected from the group consisting of a hydroxyl group and a —OM group, wherein M is a member selected from the group consisting of an alkali metal and an ammonium ion; and wherein R₂ represents a —CO-R₃ group, wherein R₃ represents the residue of any N,N-(C₁-C₂)dialkylamino acid or a C₄-C₆-cycloalkylamino acid;

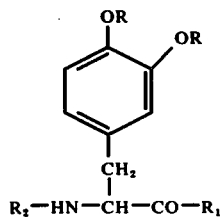
(II)

wherein R represents an acyl group; wherein R₂ represents a hydrogen atom; and wherein R₁ represents a —NHCH(R₄)COOR₅ group, wherein R₄ represents the residue of any naturally occurring protein amino acid, and wherein R₅ represents a member selected from the group consisting of a hydrogen atom, a C₁-C₅ alkyl group, and a C₁-C₅ alkylaryl group, and the HX salts thereof, wherein X is a conventional pharmaceutically acceptable acid addition salt anion;

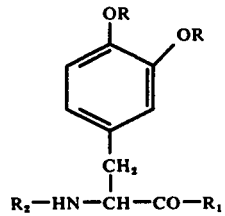
(III)

wherein R represents an acyl group; wherein R₁ represents a member selected from the group consisting of a hydroxyl group, a —OCH₃ group, a —OC₂H₅ group, a —OC₃H₇ group, a —OC₄H₉ group, and a —OCH₂—C₆H₅ group; and wherein R₂ represents an NH₂CH(R₆)CO— group, wherein R₆ represents the residue of any naturally occurring protein amino acid, and the HX salts thereof, wherein X is defined as above;

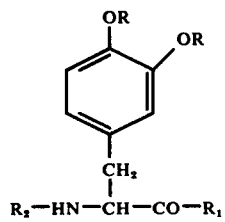
(IV)

wherein R represents a member selected from the group consisting of an acyl group; wherein R₁ represents a member selected from the group consisting of a hydroxyl group, a —OCH₃ group, a —OC₂H₅ group, a —OC₃H₇ group, a —OC₄H₉ group, and a —OCH₂-C₆H₅ group; and wherein R₂ represents an NH₂-CH(R₇)-CO— group, wherein R₇ represents the residue of a 3,4-L-diacylphenylalanine group having the formula:

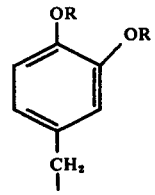

wherein R is defined as above, and the HX salts thereof, wherein X is as defined above; and

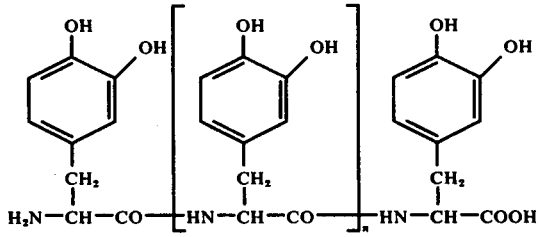
(V-A)

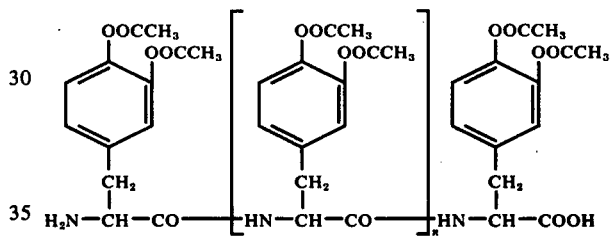
(V-B)

wherein n represents an integer of from 2 to 50 with respect to formula (V-A), and wherein n represents an integer of from 1 to 50 with respect to formula (V-B).

2. The method of claim 1, wherein said compound is: Glycyl-3,4-diacetyloxy-L-phenylalanine and its HX salt, wherein X represents a pharmaceutically acceptable anion.

3. The method of claim 1, wherein said compound is: Glycyl-3,4-diacetyloxy-L-phenylalanine-methyl ester and its HX salt, wherein X represents a pharmaceutically acceptable anion.

4. The method of claim 1, wherein said compound is: 3,4-diacetyloxy-L-phenylalanyl-glycine and its HX salt, wherein X represents a pharmaceutically acceptable anion.

5. The method of claim 1, wherein said compound is: N-nicotinoyl-3,4-dihydroxy-L-phenylalanine and its M salt, wherein M represents an alkali metal.

6. The method of claim 1, wherein said compound is: N-nicotinoyl-3,4-diacetyloxy-L-phenylalanine and its M salt, wherein M represents an alkali metal.

7. The method of claim 1, wherein said compound is: 3,4-diacetyloxy-L-phenylalanyl-glycine and its HX salt, wherein X represents a pharmaceutically acceptable anion.

8. The method of claim 1, wherein said compound is: 3,4-diacetyloxy-L-phenylalanyl-glycine-methyl ester and its HX salt, wherein X represents a pharmaceutically acceptable anion.

9. The method of claim 1, wherein said compound is:

3,4-diacetyloxy-L-phenylalanyl-glycine-ethyl ester and its HX salt, wherein X represents a pharmaceutically acceptable anion.

10. The method of claim 1, wherein said compound is:
3,4-diacetyloxy-L-phenylalanyl-glycine-benzyl ester and its HX salt, wherein X represents a pharmaceutically acceptable anion.

11. The method of claim 1, wherein said compound is:
3,4-diacetyloxy-L-phenylalanyl-L-leucine and its HX salt, wherein X represents a pharmaceutically acceptable anion.

12. The method of claim 1, wherein said compound is:
3,4-diacetyloxy-L-phenylalanyl-L-leucine-methyl ester and its HX salt, wherein X represents a pharmaceutically acceptable anion.

13. The method of claim 1, wherein said compound is:
3,4-diacetyloxy-L-phenylalanyl-L-leucine-ethyl ester and its HX salt, wherein X represents a pharmaceutically acceptable anion.

14. The method of claim 1, wherein said compound is:
3,4-diacetyloxy-L-phenylalanyl-L-leucine-benzyl ester and its HX salt, wherein X represents a pharmaceutically acceptable anion.

15. The method of claim 1, wherein said compound is:
3,4-diacetyloxy-L-phenylalanyl-L-isoleucine and its HX salt, wherein X represents a pharmaceutically acceptable anion.

16. The method of claim 1, wherein said compound is:
3,4-diacetyloxy-L-phenylalanyl-L-isoleucine-methyl ester and its HX salt, wherein X represents a pharmaceutically acceptable anion.

17. The method of claim 1, wherein said compound is:
3,4-diacetyloxy-L-phenylalanyl-L-isoleucine-ethyl ester and its HX salt, wherein X represents a pharmaceutically acceptable anion.

18. The method of claim 1, wherein said compound is:
3,4-diacetyloxy-L-phenylalanyl-L-isoleucine-benzyl ester and its HX salt, wherein X represents a pharmaceutically acceptable anion.

19. The method of claim 1, wherein said compound is:
3,4-diacetyloxy-L-phenylalanyl-phenylalanine and its HX salt, wherein X represents a pharmaceutically acceptable anion.

20. The method of claim 1, wherein said compound is:
3,4-diacetyloxy-L-phenylalanyl-phenylalanine-methyl ester and its HX salt, wherein X represents a pharmaceutically acceptable anion.

21. The method of claim 1, wherein said compound is:
3,4-diacetyloxy-L-phenylalanyl-phenylalanine-ethyl ester and its HX salt, wherein X represents a pharmaceutically acceptable anion.

22. The method of claim 1, wherein said compound is:
3,4-diacetyloxy-L-phenylalanyl-phenylalanine-benzyl ester and its HX salt, wherein X represents a pharmaceutically acceptable anion.

23. The method of claim 1, wherein said compound is:
Glycyl-3,4-diacetyloxy-L-phenylalanine and its HX salt, wherein X represents a pharmaceutically acceptable anion.

24. The method of claim 1, wherein said compound is:
Glycyl-3,4-dipivalyloxy-L-phenylalanine and its HX salt, wherein X represents a pharmaceutically acceptable anion.

25. The method of claim 1, wherein said compound:
Glycyl-3,4-diacetyloxy-L-phenylalanine-methyl ester and its HX salt, wherein X represents a pharmaceutically acceptable anion.

26. The method of claim 1, wherein said compound is:
Glycyl-3,4-diacetyloxy-L-phenylalanine-ethyl ester and its HX salt, wherein X represents a pharmaceutically acceptable anion.

27. The method of claim 1, wherein said compound is:
Glycyl-3,4-diacetyloxy-L-phenylalanine-benzyl ester and its HX salt, wherein X represents a pharmaceutically acceptable anion.

28. The method of claim 1, wherein said compound is:
L-leucyl-3,4-diacetyloxy-L-phenylalanine and its HX salt, wherein X represents a pharmaceutically acceptable anion.

29. The method of claim 1, wherein said compound is:
L-leucyl-3,4-diacetyloxy-L-phenylalanine-methyl ester and its HX salt, wherein X represents a pharmaceutically acceptable anion.

30. The method of claim 1, wherein said compound is:
L-leucyl-3,4-diacetyloxy-L-phenylalanine-ethyl ester and its HX salt, wherein X represents a pharmaceutically acceptable anion.

31. The method of claim 1, wherein said compound is:
L-leucyl-3,4-diacetyloxy-L-phenylalanine-benzyl ester and its HX salt, wherein X represents a pharmaceutically acceptable anion.

32. The method of claim 1, wherein said compound is:
L-isoleucyl-3,4-diacetyloxy-L-phenylalanine and its HX salt, wherein X represents a pharmaceutically acceptable anion.

33. The method of claim 1, wherein said compound is:
L-isoleucyl-3,4-diacetyloxy-L-phenylalanine-methyl ester and its HX salt, wherein X represents a pharmaceutically acceptable anion.

34. The method of claim 1, wherein said compound is:
L-isoleucyl-3,4-diacetyloxy-L-phenylalanine-ethyl ester and its HX salt, wherein X represents a pharmaceutically acceptable anion.

35. The method of claim 1, wherein said compound is:
L-isoleucyl-3,4-diacetyloxy-L-phenylalanine-benzyl ester and its HX salt, wherein X represents a pharmaceutically acceptable anion.

36. The method of claim 1, wherein said compound is:

Phenylalanyl-3,4-diacetyloxy-L-phenylalanine and its HX salt, wherein X represents a pharmaceutically acceptable anion.

37. The method of claim 1, wherein said compound is:
Phenylalanyl-3,4-diacetyloxy-L-phenylalanine-methyl ester and its HX salt, wherein X represents a pharmaceutically acceptable anion.

38. The method of claim 1, wherein said compound is:
Phenylalanyl-3,4-diacetyloxy-L-phenylalanine-ethyl ester and its HX salt, wherein X represents a pharmaceutically acceptable anion.

39. The method of claim 1, wherein said compound is:
Phenylalanyl-3,4-diacetyloxy-L-phenylalanine-benzyl ester and its HX salt, wherein X represents a pharmaceutically acceptable anion.

40. The method of claim 1, wherein said compound is:
3,4-diacetyloxy-L-phenylalanyl-3,4-diacetyloxy-L-phenylalanine and its HX salt, wherein X represents a pharmaceutically acceptable anion.

41. The method of claim 1, wherein said compound is:
3,4-diacetyloxy-L-phenylalanyl-3,4-diacetyloxy-L-phenylalanine-methyl ester and its HX salt, wherein X represents a pharmaceutically acceptable anion.

42. The method of claim 1, wherein said compound is:
3,4-diacetyloxy-L-phenylalanyl-3,4-diacetyloxy-L-phenylalanine-ethyl ester and its HX salt, wherein X represents a pharmaceutically acceptable anion.

43. The method of claim 1, wherein said compound is:
3,4-diacetyloxy-L-phenylalanyl-3,4-diacetyloxy-L-phenylalanine-benzyl ester and its HX salt, wherein X represents a pharmaceutically acceptable anion.

44. The method of claim 1, wherein said compound is:
Poly-3,4-dihydroxy-L-phenylalanine:

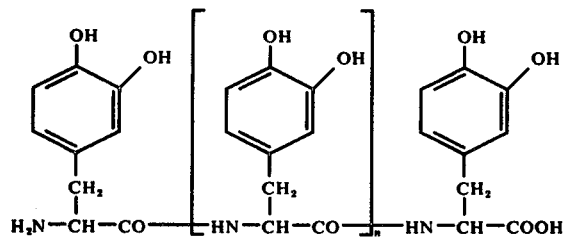

wherein n represents an integer of 7 - 20.

45. The method of claim 1, wherein said compound is:
Poly-3,4-diacetoxy-L-phenylalanine:

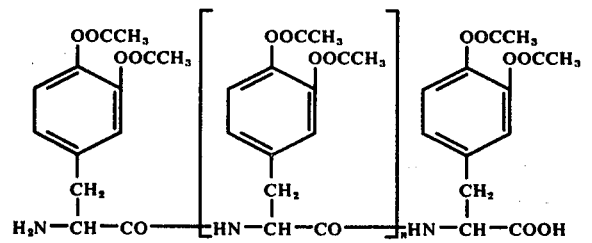

wherein n represents an integer of 7 - 20.

46. The method of claim 1, wherein said compound is:
N-[N,N-dimethylamino]-glycyl-3,4-dihydroxy-L-phenyl-alanine and its M salt, wherein M represents an alkali metal.

47. The method of claim 1, wherein said compound is:
N-[N,N-dimethylamino]-glycyl-3,4-diacetyloxy-L-phenylalanine and its M salt, wherein M represents an alkali metal.

48. The method of claim 1, wherein said compound is:
N-nicotinoyl-3,4-dinicotinoyloxy-L-phenylalanine and its M salt, wherein M represents an alkali metal.

49. The method of claim 1, wherein said compound is:
N-3-pyridylacetyl-3,4-dihydroxy-L-phenylalanine and its M salt, wherein M represents an alkali metal.

50. The method of claim 1, wherein said compound is:
N-3-pyridylacetyl-3,4-diacetyloxy-L-phenylalanine and its M salt, wherein M represents an alkali metal.

51. The method of claim 1, wherein said compound is:
3,4-N,N-dimethylaminoglycyl-L-phenylalanine methyl ester and its HX salt, wherein X represents a pharmaceutically acceptable anion.

52. The method of claim 1, wherein said compound is:
N-[N,N-dimethylamino]glycyl-3,4-[N,N-dimethylaminoglycyl]-L-phenylalanine and its M salt, wherein M represents an alkali metal.

53. The method of claim 1, wherein said compound is:
N-[N,N-dimethylaminoglycyl]-3,4-diacetyloxy-L-phenyl-alanine and its M salt, wherein M represents an alkali metal.

54. The method of claim 1, wherein said compound is:
N-nicotinoyl-3,4-dipivalyloxy-L-phenylalanine and its M salt, wherein M represents an alkali metal.

55. The method of claim 1, wherein in formula (II), said $C_1$–$C_5$ alkylaryl group is a member selected from the group consisting of a —$CH_2$-$C_6H_5$ group, and a —$CH_2$-$CH_2$-$C_6$5 group.

56. An orally administered pharmaceutical composition useful in the treatment of Parkinson's Disease which comprises an anti-Parkinsonism effective amount of a compound having the formula:

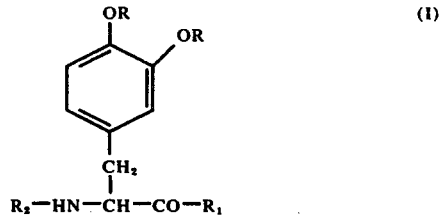

(I)

wherein R represents a hydrogen atom, an acyl group and a —CO-$R_3$ group, wherein $R_3$ represents the residue of any N,N-$C_1$-$C_2$ dialkyl-amino acid or a $C_4$–$C_6$ cycloalkylamino acid; wherein $R_1$ represents a member selected from the group consisting of a hydroxyl group and a —OM group, wherein M is a member selected from the group consisting of an alkali metal and an ammonium ion; and wherein $R_2$ represents a —CO-$R_3$ group, wherein $R_3$ represents the residue of any N,N-($C_1$-$C_2$)dialkylamino acid or a $C_4$-$C_6$-cycloalkylamino acid;

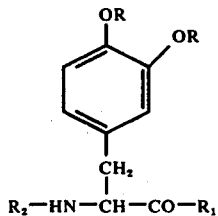
(II)

wherein R represents an acyl group; wherein $R_2$ represents a hydrogen atom; and wherein $R_1$ represents a -NHCH($R_4$)COO$R_5$ group, wherein $R_4$ represents the residue of any naturally occurring protein amino acid, and wherein $R_5$ represents a member selected from the group consisting of a hydrogen atom, a $C_1$-$C_5$ alkyl group, and a $C_1$-$C_5$ alkylaryl group, and the HX salts thereof, wherein X is a conventional pharmaceutically acceptable acid addition salt anion;

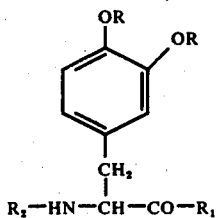
(III)

wherein R represents an acyl group; wherein $R_1$ represents a member selected from the group consisting of a hydroxyl group, a —OCH$_3$ group, a —OC$_2$H$_5$ group, a —OC$_3$H$_7$ group, a —OC$_4$H$_9$ group, and a —OCH$_2$C$_6$H$_5$ group; and wherein $R_2$ represents an NH$_2$CH(R$_6$)CO- group, wherein $R_6$ represents the residue of any naturally occurring protein amino acid, and the HX salts thereof, wherein X is defined as above;

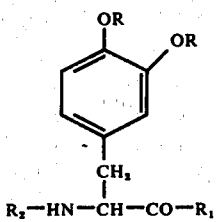
(IV)

wherein R represents a member selected from the group consisting of an acyl group; wherein $R_1$ represents a member selected from the group consisting of a hydroxyl group, a —OCH$_3$ group, a —OC$_2$H$_5$ group, a —OC$_3$H$_7$ group, a —OC$_4$H$_9$ group, and a —OCH$_2$—C$_6$H$_5$ group; and wherein $R_2$ represents an NH$_2$-CH($R_7$)—CO— group, wherein $R_7$ represents the residue of a 3,4-L-diacylphenylalanine group having the formula:

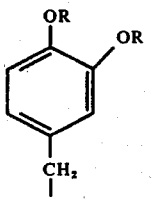

wherein R is defined as above, and the HX salts thereof, wherein X is as defined above; and

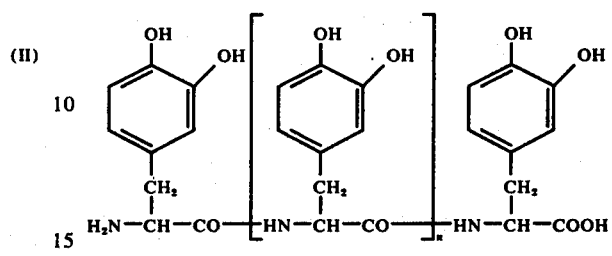
(V-A)

(V-B)

wherein n represents an integer of from 2 to 50 with respect to formula (V-A), and wherein N represents an integer of from 1 to 50 with respect to formula (V-B), in combination with an orally acceptable pharmaceutical inert carrier.

57. The compositio of claim 56 wherein said compound is:

Glycyl-3,4-diacetyloxy-L-phenylalanine and its HX salt, wherein X represents a pharmaceutically acceptable anion.

58. The composition of claim 56, wherein said compound is:

Glycyl-3,4-diacetyloxy-L-phenylalanine-methyl ester and its HX salt, wherein X represents a pharmaceutically acceptable anion.

59. The composition of claim 56, wherein said compound is:

3,4-diacetyloxy-L-phenylalanyl-glycine and its HX salt, wherein X represents a pharmaceutically acceptable anion.

60. The composition of claim 56, wherein said compound is:

N-nicotinoyl-3,4-dihydroxy-L-phenylalanine and its M salt, wherein M represents an alkali metal.

61. The composition of claim 56, wherein said compound is:

N-nicotinoyl-3,4-diacetyloxy-L-phenylalanine and its M salt, wherein M represents an alkali metal.

62. The composition of claim 56, wherein said compound is:

3,4-diacetyloxy-L-phenylalanyl-glycine and its HX salt, wherein X represents pharmaceutically acceptable anion.

63. The composition of claim 56, wherein said compound is:

3,4-diacetyloxy-L-phenylalanyl-glycine-methyl ester and its HX salt, wherein X represents a pharmaceutically acceptable anion.

64. The composition of claim 56, wherein said compound is:
3,4-diacetyloxy-L-phenylalanyl-glycine-ethyl ester and its HX salt, wherein X represents a pharmaceutically acceptable anion.

65. The composition of claim 56, wherein said compound is:
3,4-diacetyloxy-L-phenylalanyl-glycine-benzyl ester and its HX salt, wherein K represents a pharmaceutically acceptable anion.

66. The composition of claim 56, wherein said compound is:
3,4-diacetyloxy-L-phenylalanyl-L-leucine and its HX salt, wherein X represents a pharmaceutically acceptable anion.

67. The composition of claim 56, wherein said compound is:
3,4-diacetyloxy-L-phenylalanyl-L-leucine-methyl ester and its HX salt, wherein X represents a pharmaceutically acceptable anion.

68. The composition of claim 56, wherein said compound is:
3,4-diacetyloxy-L-phenylalanyl-L-leucine-ethyl ester and its HX salt, wherein X represents a pharmaceutically acceptable anion.

69. The composition of claim 56, wherein said compound is:
3,4-diacetyloxy-L-phenylalanyl-L-leucine-benzyl ester and its HX salt, wherein X represents a pharmaceutically acceptable anion.

70. The composition of claim 56, wherein said compound is:
3,4-diacetyloxy-L-phenylalanyl-L-isoleucine and its HX salt, wherein X represents a pharmaceutically acceptable anion.

71. The composition of claim 56, wherein said compound is:
3,4-diacetyloxy-L-phenylalanyl-L-isoleucine-methyl ester and its HX salt, wherein X represents a pharmaceutically acceptable anion.

72. The composition of claim 56, wherein said compound is:
3,4-diacetyloxy-L-phenylalanyl-L-isoleucine-ethyl ester and its HX salt, wherein X represents a pharmaceutically acceptable anion.

73. The composition of claim 56, wherein said compound is:
3,4-diacetyloxy-L-phenylalanyl-L-isoleucine-benzyl ester and its HX salt, wherein X represents a pharmaceutically acceptable anion.

74. The composition of claim 56, wherein said compound is:
3,4-diacetyloxy-L-phenylalanyl-phenylalanine and its HX salt, wherein X represents a pharmaceutically acceptable anion.

75. The composition of claim 56, wherein said compound is:
3,4-diacetyloxy-L-phenylalanyl-phenylalanine-methyl ester and its HX salt, wherein X represents a pharmaceutically acceptable anion.

76. The composition of claim 56, wherein said compound is:
3,4-diacetyloxy-L-phenylalanyl-phenylalanine-ethyl ester and its HX salt, wherein X represents a pharmaceutically acceptable anion.

77. The composition of claim 56, wherein said compound is:
3,4-diacetyloxy-L-phenylalanyl-phenylalanine-benzyl ester and its HX salt, wherein X represents a pharmaceutically acceptable anion.

78. The composition of claim 56, wherein said compound is:
Glycyl-3,4-diacetyloxy-L-phenylalanine and its HX salt, wherein X represents a pharmaceutically acceptable anion.

79. The composition of claim 56, wherein said compound is:
Glycyl-3,4-dipivalyloxy-L-phenylalanine and its HX salt, wherein X represents a pharmaceutically acceptable anion.

80. The composition of claim 56, wherein said compound is:
Glycyl-3,4-diacetyloxy-L-phenylalanine-methyl ester and its HX salt, wherein X represents a pharmaceutically acceptable anion.

81. The composition of claim 56, wherein said compound is:
Glycyl-3,4-diacetyloxy-L-phenylalanine-ethyl ester and its HX salt, wherein X represents a pharmaceutically acceptable anion.

82. The composition of claim 56, wherein said compound is:
Glycyl-3,4-diacetyloxy-L-phenylalanine-benzyl ester and its HX salt, wherein X represents a pharmaceutically acceptable anion.

83. The composition of claim 56, wherein said compound is:
L-leucyl-3,4-diacetyloxy-L-phenylalanine and its HX salt, wherein X represents a pharmaceutically acceptable anion.

84. The composition of claim 56, wherein said compound is:
L-leucyl-3,4-diacetyloxy-L-phenylalanine-methyl ester and its HX salt, wherein X represents a pharmaceutically acceptable anion.

85. The composition of claim 56, wherein said compound is:
L-leucyl-3,4-diacetyloxy-L-phenylalanine-ethyl ester and its HX salt, wherein X represents a pharmaceutically acceptable anion.

86. The composition of claim 56, wherein said compound is:
L-leucyl-3,4-diacetyloxy-L-phenylalanine-benzyl ester and its HX salt, wherein X represents a pharmaceutically acceptable anion.

87. The composition of claim 56, wherein said compound is:
L-isoleucyl-3,4-diacetyloxy-L-phenylalanine and its HX salt, wherein X represents a pharmaceutically acceptable anion.

88. The composition of claim 56, wherein said compound is:
L-isoleucyl-3,4-diacetyloxy-L-phenylalanine-methyl ester and its HX salt, wherein X represents a pharmaceutically acceptable anion.

89. The composition of claim 56, wherein said compound is:
L-isoleucyl-3,4-diacetyloxy-L-phenylalanine-ethyl ester and its HX salt, wherein X represents a pharmaceutically acceptable anion.

90. The composition of claim 56, wherein said compound is:

L-isoleucyl-3,4-diacetyloxy-L-phenylalanine-benzyl ester and its HX salt, wherein X represents a pharmaceutically acceptable anion.

91. The composition of claim 56, wherein said compound is:
Phenylalanyl-3,4-diacetyloxy-L-phenylalanine and its HX salt, wherein X represents a pharmaceutically acceptable anion.

92. The composition of claim 56, wherein said compound is:
Phenylalanyl-3,4-diacetyloxy-L-phenylalanine-methyl ester and its HX salt, wherein X represents a pharmaceutically acceptable anion.

93. The composition of claim 56, wherein said compound is:
phenylalanyl-3,4-diacetyloxy-phenylalanine-ethyl ester and its HX salt, wherein X represents a pharmaceutically acceptable anion.

94. The composition of claim 56, wherein said compound is:
Phenylalanyl-3,4-diacetyloxy-L-phenylalanine-benzyl ester and its HX salt, wherein X represents a pharmaceutically acceptable anion.

95. The composition of claim 56, wherein said compound is:
3,4-diacetyloxy-L-phenylalanyl-3,4-diacetyloxy-L-phenylalanine and its HX salt, wherein X represents a pharmaceutically acceptable anion.

96. The composition of claim 56, wherein said compound is:
3,4-diacetyloxy-L-phenylalanyl-3,4-diacetyloxy-L-phenylalanine-methyl ester and its HX salt, wherein X represents a pharmaceutically acceptable anion.

97. The composition of claim 56, wherein said compound is:
3,4-diacetyloxy-L-phenylalanyl-3,4-diacetyloxy-L-phenylalanine-ethyl ester and its HX salt, wherein X represents a pharmaceutically acceptable anion.

98. The composition of claim 56, wherein said compound is:
3,4-diacetyloxy-L-phenylalanyl-3,4-diacetyloxy-L-phenylalanine-benzyl ester and its HX salt, wherein X represents a pharmaceutically acceptable anion.

99. The composition of claim 56, wherein said compound is:
Poly-3,4-dihydroxy-L-phenylalanine:

wherein $n$ represents an integer of 7 – 20.

100. The composition of claim 56, wherein said compound is:
Poly-3,4-diacetyloxy-L-phenylalanine:

wherein $n$ represents an integer of 7 – 20.

101. The composition of claim 56, wherein said compound is:
N-[N,N-dimethylamino]-glycyl-3,4-dihydroxy-L-phenylalanine and its M salt, wherein M represents an alkali metal.

102. The composition of claim 56, wherein said compound is:
N-[N,N-dimethylamino]-glycyl-3,4-diacetyloxy-L-phenylalanine and its M salt, wherein M represents an alkali metal.

103. The composition of claim 56, wherein said compound is:
N-nicotinoyl-3,4-dinicotinoyloxy-L-phenylalanine and its M salt, wherein M represents an alkali metal.

104. The composition of claim 56, wherein said compound is:
N-3-pyridylacetyl-3,4-dihydroxy-L-phenylalanine and its M salt, wherein M represents an alkali metal.

105. The composition of claim 56, wherein said compound is:
N-3-pyridylacetyl-3,4-diacetyloxy-L-phenylalanine and its M salt, wherein M represents an alkali metal.

106. The composition of claim 56, wherein said compound is:
3,4-N,N-dimethylaminoglycyl-L-phenylalanine methyl ester and its HX salt, wherein X represents a pharmaceutically acceptable anion.

107. The composition of claim 56, wherein said compound is:
N-[N,N-dimethylamino]glycyl-3,4-[N,N-dimethylamino-glycyl]-L-phenylalanine and its M salt, wherein M represents an alkali metal.

108. The composition of claim 56, wherein said compound is:
N-[N,N-diethylaminoglycyl]-3,4-diacetyloxy-L-phenyl-alanine and its M salt, wherein M represents an alkali metal.

109. The composition of claim 56, wherein in formula (II), said $C_1$–$C_5$ alkylaryl group is a member selected from the group consisting of a —$CH_2$-$C_6H_5$ group, and a —$CH_2$-$CH_2$-$C_6H_5$ group.

* * * * *